(12) United States Patent
Tanabe

(10) Patent No.: US 10,628,026 B2
(45) Date of Patent: Apr. 21, 2020

(54) MEDICAL IMAGE DISPLAY DEVICE, TOUCH OPERATION CONTROL PROGRAM, AND TOUCH OPERATION CONTROL METHOD

(71) Applicant: Konica Minolta, Inc., Tokyo (JP)

(72) Inventor: Yusuke Tanabe, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/967,741

(22) Filed: May 1, 2018

(65) Prior Publication Data

US 2018/0348983 A1    Dec. 6, 2018

(30) Foreign Application Priority Data

Jun. 2, 2017    (JP) .................................. 2017-109751

(51) Int. Cl.
| | | |
|---|---|---|
| *A61B 6/00* | (2006.01) | |
| *G06F 3/0488* | (2013.01) | |
| *G06F 3/0484* | (2013.01) | |
| *A61B 8/00* | (2006.01) | |

(52) U.S. Cl.
CPC .............. *G06F 3/0488* (2013.01); *A61B 8/46* (2013.01); *A61B 8/467* (2013.01); *G06F 3/04842* (2013.01); *G06F 3/04845* (2013.01); *G06F 3/04883* (2013.01)

(58) Field of Classification Search
CPC ................................ A61B 8/467; G06F 3/016

USPC ........................................ 600/443; 340/407.2
See application file for complete search history.

(56) References Cited

U.S. PATENT DOCUMENTS

2009/0289779 A1* 11/2009 Braun ..................... G06F 3/016
                                                        340/407.2
2013/0324850 A1* 12/2013 Petruzzelli ............. A61B 8/467
                                                        600/443

FOREIGN PATENT DOCUMENTS

| JP | 2012019824 A | 2/2012 |
| JP | 5371798 B2 | 9/2013 |

* cited by examiner

*Primary Examiner* — Abdul-Samad A Adediran
(74) *Attorney, Agent, or Firm* — Lucas & Mercanti, LLP

(57) ABSTRACT

A medical image display device having a touch panel that displays a medical image, includes: a hardware processor that accepts an operation on the touch panel and detects a drag operation on a mark corresponding to a function selected from a plurality of functions; calculates a movement position of the mark according to a rule corresponding to at least one of the selected function, an object, and a user based on coordinates of a touch position in the drag operation; and causes the touch panel to display the medical image and the mark and to move the mark on the medical image based on the calculated movement position, wherein the hardware processor calculates the movement position of the mark such that a movement trajectory of the touch position and a movement trajectory of the mark are different from each other.

25 Claims, 18 Drawing Sheets

10

| FUNCTION | MARK |
|---|---|
| ANNOTATION FUNCTION | ◄ ━━ |
| MEASUREMENT FUNCTION | ✚ | r0: DISTANCE FROM CENTER OF MARK x0, y0: DISTANCES FROM CENTER OF PROBE MARK

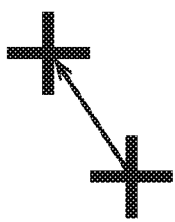
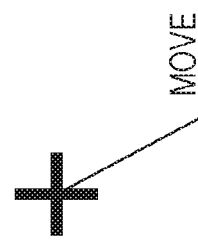
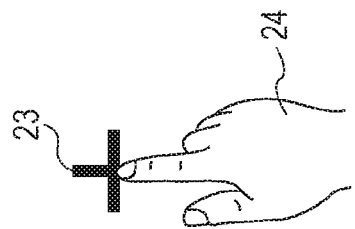
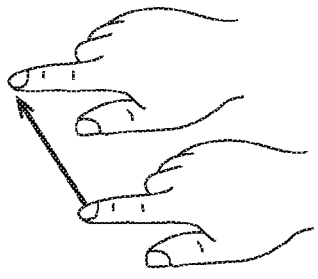
FIG. 17A  SELECT BY TOUCHING MARK
FIG. 17B  MOVE FINGER WITHIN PREDETERMINED TIME
FIG. 17C  DRAG OPERATION

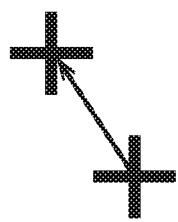 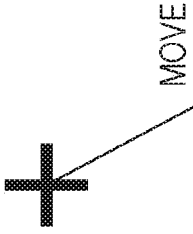 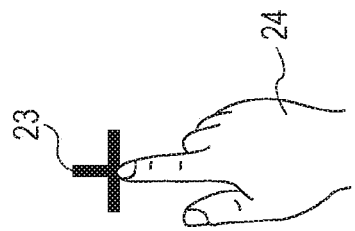
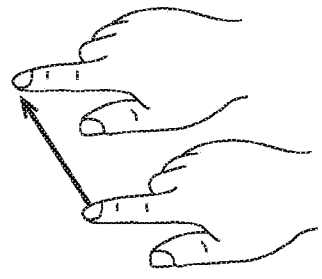 
FIG. 18A — SELECT BY TOUCHING MARK
FIG. 18B — MOVE FINGER AND THEN STOP FINGER FOR PREDETERMINED TIME
FIG. 18C — DRAG OPERATION

WHEN MARK CANNOT BE MOVED

WHEN MARK CAN BE MOVED

MEDICAL IMAGE DISPLAY DEVICE, TOUCH OPERATION CONTROL PROGRAM, AND TOUCH OPERATION CONTROL METHOD

The entire disclosure of Japanese patent Application No. 2017-109751, filed on Jun. 2, 2017, is incorporated herein by reference in its entirety.

BACKGROUND

Technological Field

The present invention relates to a medical image display device, a touch operation control program, and a touch operation control method. In particular, the present invention relates to a medical image display device having a touch panel that displays a medical image, a touch operation control program that controls a touch operation on the touch panel of the medical image display device, and a touch operation control method.

Description of the Related Art

With the widespread use of touch panels in recent years, the number of medical image display devices using a touch panel such as ultrasonic diagnostic devices has been increasing. Various diagnoses are performed by, for example, measuring various kinds of information on medical images and providing annotations on medical images by operating a touch panel.

Regarding such a touch operation in a medical image display device, for example, JP 2012-019824 A discloses an ultrasonic diagnostic device including a diagnostic image forming unit that forms a diagnostic image based on a received signal obtained by transmitting and receiving ultrasonic waves, a display image forming unit that forms a display image provided with a target point marker indicating a target position of an operation and an operation button associated with the target point marker in the diagnostic image, a display part that displays the display image and senses a touch operation on the display image, and a controller that accepts an operation on the target point marker via a touch operation on the operation button associated with the target point marker.

JP 5371798 B2 discloses a technique related to a touch operation in an information processing apparatus for moving an object displayed on a display screen on the display screen although the technique is not related to a medical image display device. The information processing apparatus includes an input unit that inputs coordinates instructed for the display screen, a selection unit that selects the object being displayed at a coordinate position on the display screen corresponding to the input coordinates that were input by the input unit, a detecting unit that detects, based on the input coordinates, a drag operation on the object selected by the selection unit, a determination unit that determines, when the detection unit detects the drag operation, whether a distance between the coordinate position of the object selected by the selection unit and the input coordinates after detection of the drag operation exceeds a predetermined distance, and a movement controller that moves the object selected by the selection unit to follow the drag operation, wherein when the distance does not exceed the predetermined distance, the movement controller sets a movement amount of the object selected by the selection unit smaller than a movement amount of the drag operation.

Unlike a normal device such as a tablet having a touch panel, a medical image display device requires a precise touch operation for using functions such as measurement and annotation. When various marks are moved on a medical image via a touch operation, an object (a mark or a medical image in the vicinity of the mark) is hidden by touching means such as a finger to deteriorate the visibility of the object, which is a serious problem. Therefore, in a medical image display device having a touch panel, a touch operation method allowing a precise operation while securing the visibility of an object is strongly required.

In order to solve this problem, JP 2012-019824 A provides operation buttons in the vicinity of a target point marker to prevent the object from being hidden by the finger. However, in this method, part of an object is hidden by the operation buttons provided in the vicinity of a target point marker to deteriorate the visibility, which is a problem. Especially when there are multiple annotations such as letters and arrows on the screen, this problem is remarkable. In addition, JP 5371798 B2 proposes a method of defining an area around an object and keeping the object where it is (or moving the object only a little) within the area. This makes the object move lagging behind a finger performing the drag, thereby improving the visibility of the object. However, this method has a problem that fine adjustment of an object is difficult because a movement amount of the object abruptly changes when a finger that performs drag moves out of the area. That is, this method is not appropriate in situations where precision of a touch operation is required such as measurement.

SUMMARY

The present invention has been made in view of the above problems, and its main object is to provide a medical image display device, a touch operation control program, and a touch operation control method capable of suppressing deterioration of the visibility of an object in a touch operation and appropriately controlling the touch operation according to a function.

To achieve the abovementioned object, according to an aspect of the present invention, a medical image display device having a touch panel that displays a medical image, reflecting one aspect of the present invention comprises: a hardware processor that accepts an operation on the touch panel and detects a drag operation on a mark corresponding to a function selected from a plurality of functions; calculates a movement position of the mark according to a rule corresponding to at least one of the selected function, an object, and a user based on coordinates of a touch position in the drag operation; and causes the touch panel to display the medical image and the mark and to move the mark on the medical image based on the calculated movement position, wherein the hardware processor calculates the movement position of the mark such that a movement trajectory of the touch position and a movement trajectory of the mark are different from each other.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIGS. 17A to 17C are schematic diagrams illustrating a method of moving a mark (a caliper when the measurement function is selected) on the touch panel of the medical image display device according to the embodiment of the present invention;

FIGS. 18A to 18C are schematic diagrams illustrating a method of moving the mark (the caliper when the measurement function is selected) on the touch panel of the medical image display device according to the embodiment of the present invention;

DETAILED DESCRIPTION OF EMBODIMENTS

Figure 1:
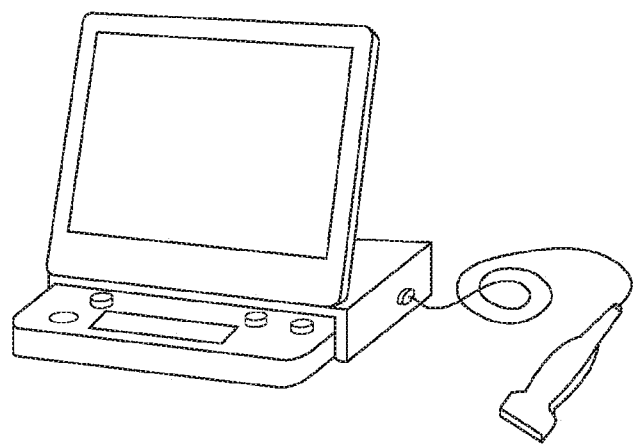
FIG. 1 is an external view illustrating a medical image display device according to an embodiment of the present invention.

Hereinafter, one or more embodiments of the present invention will be described with reference to the drawings. However, the scope of the invention is not limited to the disclosed embodiments.

As described in the description of the related art, the number of medical image display devices using a touch panel has been increasing. Unlike a normal apparatus such as a tablet having a touch panel, a precise touch operation is required for a medical image display device when functions including measurement and annotation are used. However, when a mark corresponding to a function is moved on a medical image by a touch operation, an object (a mark or a medical image in the vicinity of the mark) may be hidden by the touching means such as a finger, and the visibility of the object is deteriorated, which is a serious problem.

To solve this problem, in JP 2012-019824 A, an operation button is provided in the vicinity of a target point marker to prevent an object from being hidden by a finger. In this method, however, part of the object is hidden by the operation button, and the visibility thereof is deteriorated. This problem appears clearly especially when there are a plurality of annotations such as letters and arrows on the screen. In addition, in JP 5371798 B2, an area is defined around an object, and in the area, movement of the object is limited to improve the visibility of the object. However, in this method, a movement amount of the object abruptly changes when a finger that performs drag moves out of the area, which makes fine adjustment difficult. Thus, this method cannot be used in a situation where precision of a touch operation is required such as measurement.

Therefore, in one embodiment of the present invention, the behavior of a touch operation is changed according to scenes defined by a function to be used, an object, a user, etc. to improve the visibility of the object (a mark or a medical image in the vicinity of the mark). Specifically, when a medical image and marks corresponding to various functions are displayed on a touch panel, and a mark is moved on the medical image by a touch operation, upon detection of a drag operation on the mark, a movement position of the mark is calculated such that the movement trajectory of the touch position and the movement trajectory of the mark are different from each other based on the coordinates of the touch position in the drag operation, and the mark is moved on the medical image based on the calculated movement position, whereby the visibility of an object is improved. At that time, depending on a function to be used, an object, and a user, precision may be or may not be important. Especially when a measurement function is used, precision is required most. For a measurement function, improvement of visibility is meaningless if precision is deteriorated. Therefore, the behavior of a touch operation is changed according to at least one of a function being used, an object, and a user, whereby a touch operation suitable for the scene is made possible.

For example, when a mark corresponding to the annotation function is displayed, the touch position on the mark is used as a start point of a drag operation and the movement position of the mark is calculated such that the movement distance of the mark is smaller than the movement distance of the touch position. At that time, the closer the mark and the touching means (finger) are, the worse the visibility of the object becomes. Therefore, when the touch position is within a predetermined area around a center of the mark, the movement distance of the mark is calculated to be smaller than the movement distance of the touch position. With this operation, when the mark and the finger are close to each other, the mark and the finger tend to separate from each other, so that the object can be prevented from being hidden by the finger, and when the mark and the finger are far from each other, the movement amount of the mark becomes large, so that the operator can easily grasp the movement amount of the mark with the senses, and the operability can be improved. In addition, since the drag direction in which the visibility of the object is deteriorated is different depending on a dominant hand of a user, when the touch position moves in the upward direction and opposite of the dominant hand in the left-right direction on the touch panel, the movement amount the mark is calculated to be smaller than the movement amount of the touch position. With this operation, the touch operation can be appropriately controlled according to an operator.

In addition, when the mark corresponding to the measurement function is displayed, a position associated with a touch position on the mark (when the touch position moves before a predetermined time elapses since the time when the touch is detected, the position is the movement destination of the touch position, and when the touch position does not move before the predetermined time elapses, the position is the movement destination) is used as a start point of a drag operation and the mark is moved corresponding to the movement of the touch position. At that time, the shorter the elapsed time from setting the start point of the drag operation gets, the worse the visibility of the object becomes. Therefore, from the time when a start point of a drag operation is set to the time when a predetermined time has elapsed, the movement position of the mark is calculated such that the movement amount of the mark is smaller than the movement amount of the touch position. With this operation, when the mark and the finger are close to each other, the mark and the finger tend to separate from each other, so that the object can be prevented from being hidden by the finger, and when the mark and the finger are far from each other, the movement amount of the mark becomes large, so that the operator can easily grasp the movement amount of the mark with the senses, and the operability can be improved. Further, when the touch operation is controlled according to time, the display form of the mark is changed according to the elapsed time because the elapsed time is difficult to be recognized. As a result, it is possible to determine whether a touch operation is possible by looking at the mark, so that an erroneous operation can be prevented in advance.

Embodiment

Figure 2A:
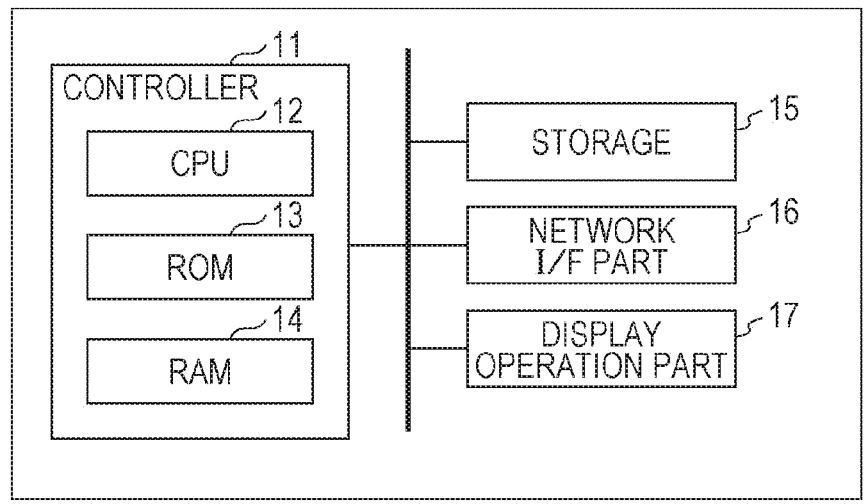
FIGS. 2A and 2B are block diagrams illustrating a configuration of the medical image display device according to the embodiment of the present invention.
Figure 2B:
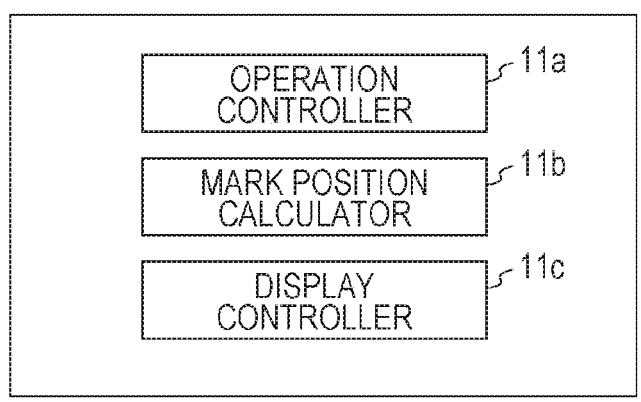

In order to describe the embodiment of the present invention described above in further detail, a medical image display device, a touch operation control program, and a touch operation control method according to the embodiment of the present invention will be described with reference to FIGS. 1 to 20B. FIG. 1 is an external view illustrating a medical image display device of the present embodiment, and FIGS. 2A and 2B are block diagrams illustrating a configuration of the medical image display device. FIGS. 3 to 7 are flowchart diagrams illustrating operations of the medical image display device, and FIG. 8 is an example of a display screen displayed on a touch panel of the medical image display device. FIG. 9 is an example of marks corresponding to functions of the medical image display device, and FIGS. 10 to 20B are diagrams for describing movement of the marks corresponding to the functions of the medical image display device.

As illustrated in FIG. 1, the medical image display device 10 of the present embodiment is, for example, an ultrasonic diagnostic device that acquires an image obtained by measuring a patient using a probe that transmits and receives ultrasonic waves, has a plurality of functions such as an annotation function for providing an annotation on a medical image and a measurement function for measuring various kinds of information of a medical image, and is configured to be able to display marks corresponding to the functions.

In the present embodiment, the medical image display device 10 will be described as a single apparatus, but a measurement device for acquiring medical images and a display device for displaying the medical images may be configured separately, and the devices may be connected through a communication network such as a Local Area Network (LAN) defined by standards such as Ethernet (registered trademark), Token Ring, Fiber-Distributed Data Interface (FDDI), and the like so that the display device can receive and display medical image data acquired by the measurement device for patient diagnosis. Alternatively, the display device can acquire/display medical image data acquired by the measurement device via a Universal Serial Bus (USB) memory or the like.

As illustrated in FIG. 2A, the medical image display device 10 includes a controller 11, a storage 15, a network I/F part 16, a display operation part (touch panel) 17, and the like.

The controller 11 includes a Central Processing Unit (CPU) 12, memories such as a Read Only Memory (ROM) 13 and a Random Access Memory (RAM) 14, and these are connected via a bus. The ROM 13 stores programs and the like. The RAM 14 stores data necessary for control by the CPU 12, data that needs to be temporarily stored at the time of a control operation, and the like. The CPU 12 then loads a control program stored in the ROM 13 and the storage 15 into the RAM 14 and executes it, thereby controlling the operation of the entire medical image display device 10.

As illustrated in FIG. 2B, the controller 11 functions as an operation controller 11a, a mark position calculator 11b, a display controller 11c, and the like.

The operation controller 11a accepts a touch operation on a display operation part (touch panel) 17 by touching means (hereinafter referred to as a finger), selects a function for a medical image, specifies a mark corresponding to the selected function, sets a dominant hand of an operator, sets a start point of a drag operation on a mark, detects a drag operation, and detects a movement direction of a touch position in the drag operation. The operation controller 11a also allows setting how a movement trajectory of a mark is changed with respect to the movement trajectory of a touch position for each function, each object, and each user.

Based on the coordinates of a touch position in a drag operation, the mark position calculator 11b calculates a movement position of the mark according to a rule corresponding to at least one of the selected function, object, and user. For example, when the annotation function is selected, the movement position of the mark may be calculated such that the movement amount of the mark is smaller than the movement amount of the touch position. When the touch position is within a predetermined area around the center of the mark, the movement position of the mark may be calculated such that the movement amount of the mark is smaller than the movement amount of the touch position. When the touch position is in an upper portion of the touch panel and in a left portion or right portion that is opposite of the dominant hand of the operator in the left-right direction, the movement position of the mark may be calculated such that the movement amount of the mark is smaller than the movement amount of the touch position. When the measurement function is selected, the movement position of the mark may be calculated such that the mark moves according to the movement of the touch position, or the movement position of the mark may be calculated such that the movement amount of the mark is smaller than the movement amount of the touch position from the time when a start point of a drag operation is set to the time when a predetermined time has elapsed.

The display controller 11c displays a medical image on the display operation part 17 and displays a mark corresponding to a selected function on the medical image. When the operation controller 11a detects a drag operation, the mark is moved on the medical image based on a movement position calculated by the mark position calculator 11b.

The operation controller 11a, the mark position calculator 11b, and the display controller 11c may be configured as hardware, or the controller 11 may be configured as software (touch operation control program) that causes the controller 11 to function as the operation controller 11a, the mark position calculator 11b, and the display controller 11c, and the CPU 12 may be configured to execute the software.

The storage 15 may include a Hard Disk Drive (HDD), a Solid State Drive (SSD), or the like, and stores a program for the CPU 12 to control each unit, information on processing functions of the device that includes the storage 15, medical image data, a table for associating functions and marks, and the like.

The network I/F part 16 includes a Network Interface Card (NIC), a modem, or the like, establishes a connection with a measurement device or the like that is provided as necessary and connected via a communication network, and receives medical image data and the like.

The display operation part 17 may be a touch panel including an operation part such as a touch sensor in which transparent electrodes are arranged in a lattice pattern on a display part such as a Liquid Crystal Display (LCD) or an organic Electro Luminescence (EL) display, and the display operation part 17 enables display of medical image and marks, selection of a function, setting of a dominant hand of an operator, a drag operation of a mark according to a function, and the like.

FIGS. 1, 2A, and 2B are an example of the medical image display device 10 of the present embodiment, and the configuration and control contents thereof can be appropriately modified.

Hereinafter, the specific operation of the medical image display device 10 will be described. The CPU 12 loads the touch operation control program stored in the ROM 13 or the storage 15 into the RAM 14 and executes it, thereby executing the processing of each step illustrated in the flowchart diagrams of FIGS. 3 to 7.

Figure 3:
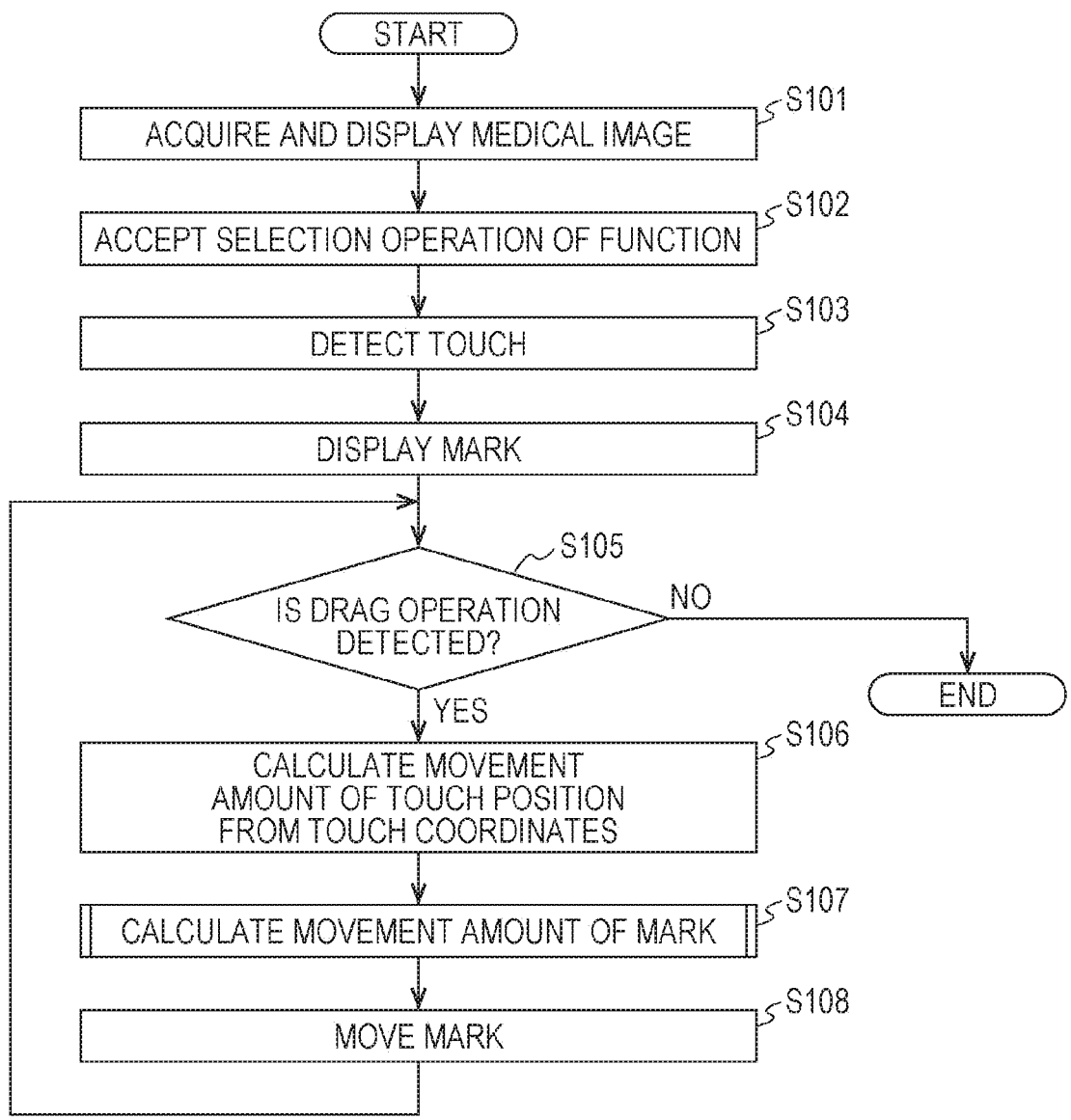
FIG. 3 is a flowchart diagram illustrating an operation of the medical image display device according to the embodiment of the present invention.

As illustrated in FIG. 3, the controller 11 (display controller 11c) of the medical image display device 10 acquires a medical image obtained by measuring a patient using a probe or the like (or a medical image obtained by measuring the patient using a measurement device), and displays, for example, a display screen 20 illustrated in FIG. 8 on the display operation part 17 (S101). The display screen 20 includes, for example, an image display field 21 in which a medical image is displayed, a setting field 22 for selecting functions, adjusting density, adjusting magnification, and the like.

Next, the controller 11 (operation controller 11a) accepts a selection operation of a function performed on the setting field 22 of the display screen 20 or the like (S102). In the present embodiment, functions of the medical image display device 10 include an annotation function for providing annotation to a medical image, a body mark function for providing a diagram indicating a part of a body that has been diagnosed, and a measurement function for measuring various kinds of information on the medical image. An operator may select a desired function by touching the touch panel or operating a trackball.

Figure 10:
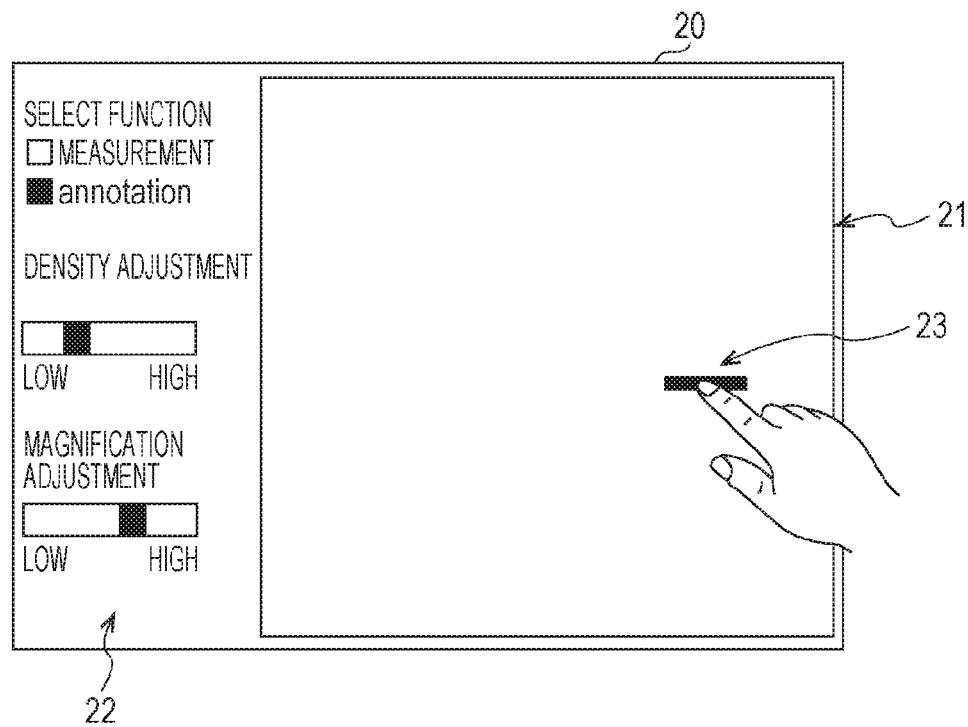
FIG. 10 is a display example of a mark (mark when an annotation function is selected) on the touch panel of the medical image display device according to the embodiment of the present invention.
Figure 11:
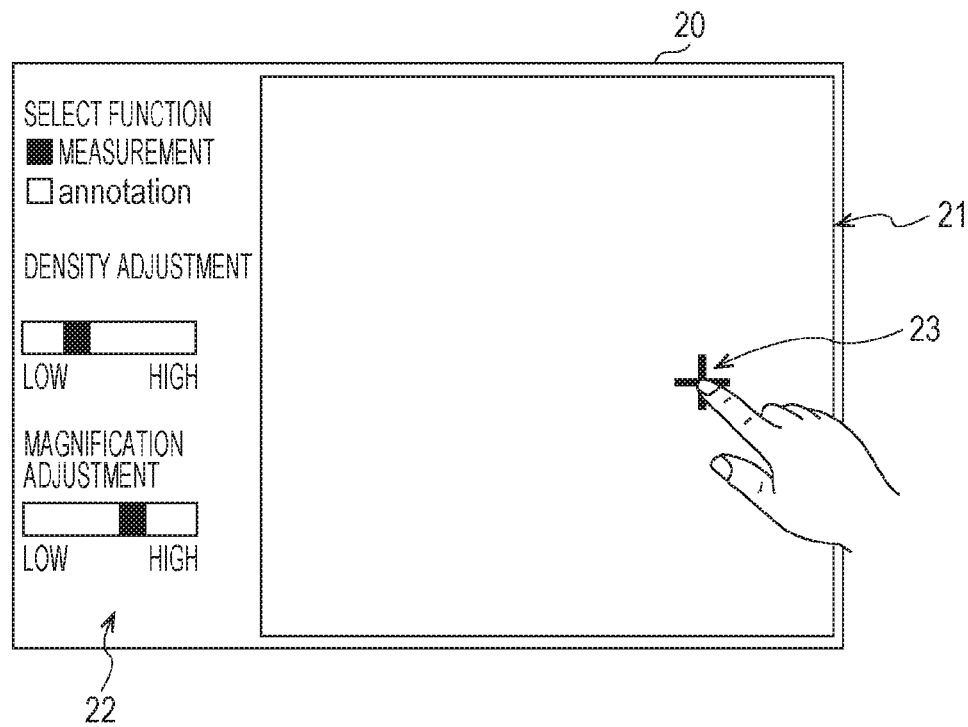
FIG. 11 is a display example of a mark (mark when a measurement function is selected) on the touch panel of the medical image display device according to the embodiment of the present invention.

The controller 11 (operation controller 11a) then monitors an output signal from the display operation part 17, and upon detection of a touch operation on the image display field 21 of the display screen 20 by an operator (S103), the controller 11 (display controller 11c) displays a mark corresponding to the function selected in S102 at the touch position (S104). FIG. 9 illustrates an example of marks corresponding to functions. When the annotation function is selected, an arrow mark or an arbitrary character string is displayed at the touch position as illustrated in FIG. 10. When the body mark function is selected, a horizontally long rectangular mark (referred to as a probe mark) is displayed in a view showing an organism. When the measurement function is selected, a cross mark (referred to as a caliper) is displayed at the touch position as illustrated in FIG. 11. In the present embodiment, when a touch operation is detected, a mark is displayed at the touch position. However, when a function is selected in S102, a mark may be displayed at a predetermined position.

Next, the controller 11 (operation controller 11a) monitors an output signal from the display operation part 17, determines whether a drag operation on the image display field 21 by an operator is detected (S105), and when a drag operation is detected (Yes in S105), the controller 11 (mark position calculator 11b) calculates a movement amount of the touch position from the coordinates of the touch position (S106), and calculates a movement amount of a mark based on the movement amount (movement position) of the touch position according to a rule according to the selected function (S107).

Figure 12A:
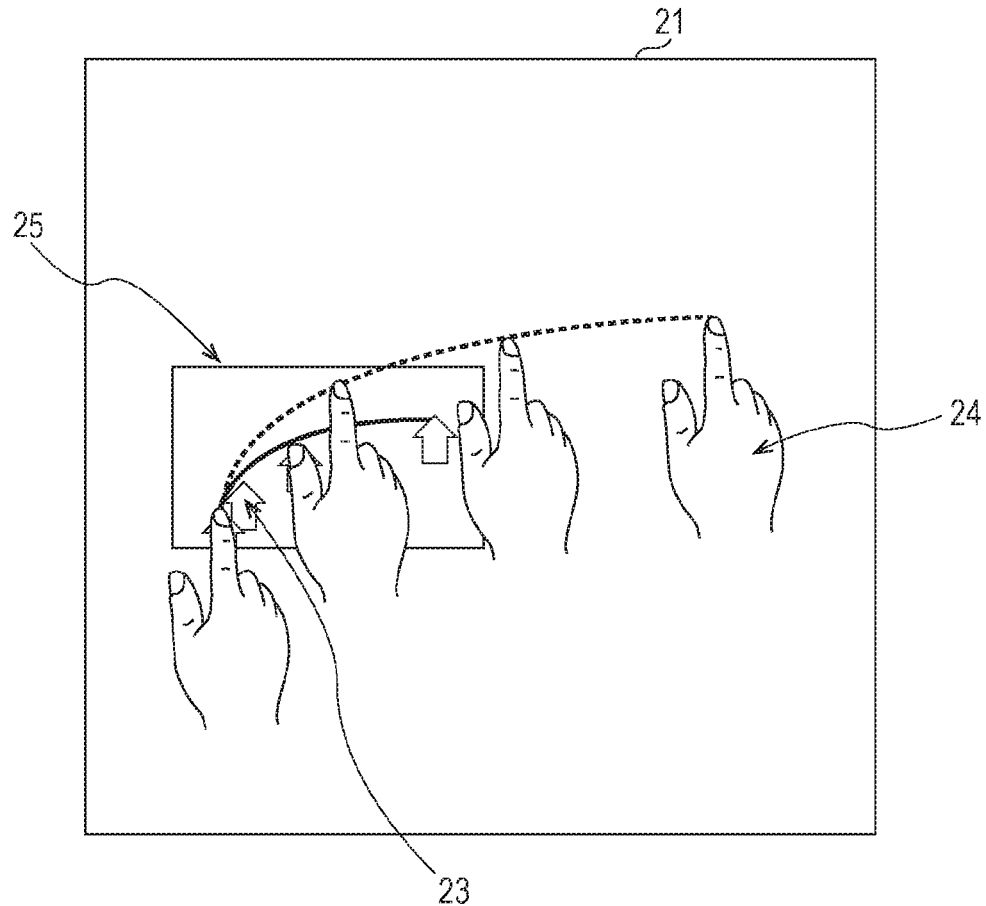
FIGS. 12A and 12B are schematic diagrams illustrating a movement trajectory of a touch position and a movement trajectory of a mark on the touch panel of the medical image display device according to the embodiment of the present invention.
Figure 12B:
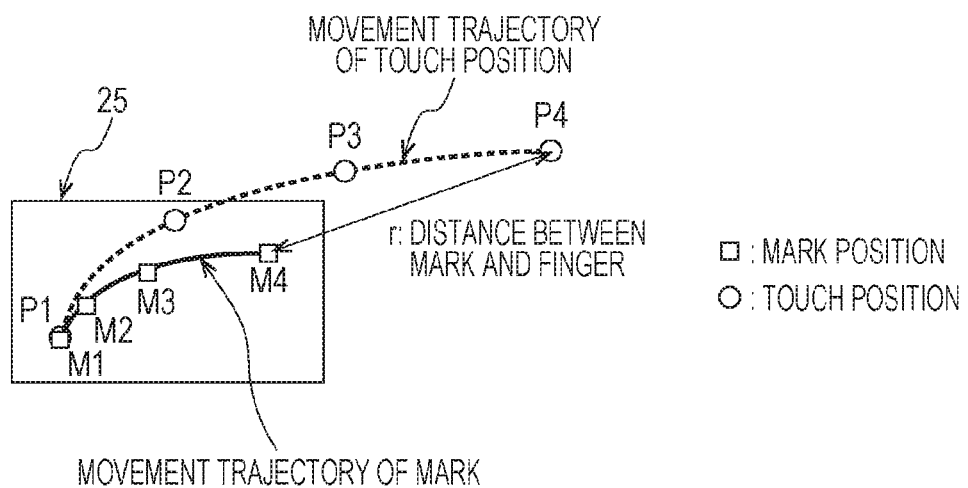

FIG. 12A illustrates a case where the lower left of an area of interest 25 in a medical image is touched with touching means 24 (a finger in this case) and the touch position is moved to the upper right. The touch position of the touching means 24 moves in the order of P1→P2→P3→P4 as illustrated in FIG. 12B. Normally, the position of a mark 23 also moves following the movement of the touch position. However, when the touching means 24 is on the mark 23, the touching means 24 hides the mark 23 and the area of interest 25 close to the mark 23. Thus, the position of the mark 23 on the area of interest 25 becomes difficult be recognized and the mark 23 cannot be accurately operated on the area of interest 25. Therefore, in the present embodiment, the movement amount (movement position) of the mark 23 is calculated such that the movement trajectory of the touch position of the touching means 24 (P1→P2→P3→P4) and the movement trajectory of the mark 23 (M1→M2→M3→M4) are different from each other.

At that time, by making the movement amount of the mark 23 smaller than the movement amount of the touch position of the touching means 24, the distance between the mark 23 and the touching means 24 is increased, so that the position of the mark 23 on the area of interest 25 can be easily recognized. Meanwhile, by making the movement amount of the mark 23 smaller than the movement amount of the touch position of the touching means 24, the touch position of the touching means 24 has to be largely moved in order to move the mark 23, which deteriorates operability.

Therefore, in the present embodiment, as illustrated in FIG. 12B, in the initial stage of the drag operation, the movement amount of the mark 23 is made small with respect to the movement of the touch position of the touching means 24 (the movement amount of M1→M2 is made small), and after the initial stage of the drag operation, the movement amount of the mark 23 is made large with respect to the movement of the touch position of the touching means 24 (the movement amount of M2→M3 and M3→M4 is made large).

Figure 13A:
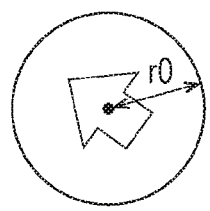
FIGS. 13A and 13B are diagrams illustrating a change in the movement amount a mark (an arrow mark when the annotation function is selected) on the touch panel of the medical image display device according to the embodiment of the present invention.

For example, when the mark 23 corresponding to the annotation function (arrow mark) is operated, an area of a distance 10 from the center of the mark 23 is set as illustrated in FIG. 13A, and the movement distance of the mark 23 is calculated using Expressions (1) and (2).

movement distance of mark 23(arrow mark)=$A$×
movement distance of touch position     (1)

$A=1/(1+a^{r0-r})$     (2)

where r is the distance between the mark 23 and the touching means 24 (finger), and a is a constant.

Figure 13B:
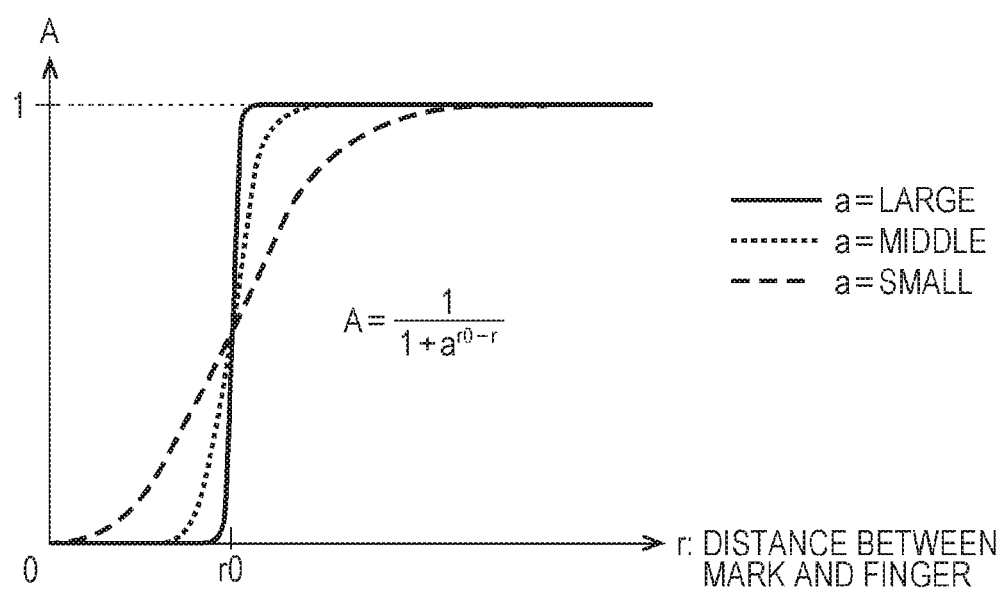

When Equation (2) is satisfied, the correlation between r and A is as illustrated in FIG. 13B, and when r is smaller than r0 (that is, the touching means 24 is in the area surrounded by the circle of FIG. 13A), A is small (approaches zero) and the movement distance of the mark 23 is small, and when r is larger than r0 (that is, the touching means 24 moves to the outside of the area surrounded by the circle of FIG. 13A), A is large (approaches one) and the movement distance of the mark 23 is large. In addition, by adjusting the value of the constant a, the degree of change of A when r is close to r0 can be adjusted. For example, when the value of the constant a is set large, the value of A can be abruptly changed when r is close to r0 as represented by the solid line in the drawing, and when the value of the constant a is set small, the value of A can be gently changed when r is close to r0 as represented by a coarse broken line in the drawing.

Figure 14A:
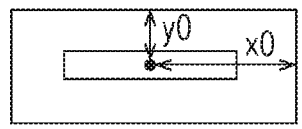
FIGS. 14A and 14B are diagrams illustrating a change in the movement amount of a mark (a probe mark when the annotation function is selected) on the touch panel of the medical image display device according to the embodiment of the present invention.

Similarly, when the mark 23 corresponding to the annotation function (probe mark) is operated, an area of a distance x0 in the x direction and a distance y0 in the y direction from the center of the mark 23 are set as illustrated in FIG. 14A, and the movement distance of the mark 23 is calculated using Expressions (3) and (4).

movement distance of mark 23(probe mark)=$A$×
movement distance of touch position     (3)

$A=1/(1+a^{x0-x})$ or $A=1/(1+a^{y0-y})$     (4)

where x (or y) is the distance between the mark 23 and the touching means 24, and a is a constant.

Figure 14B:
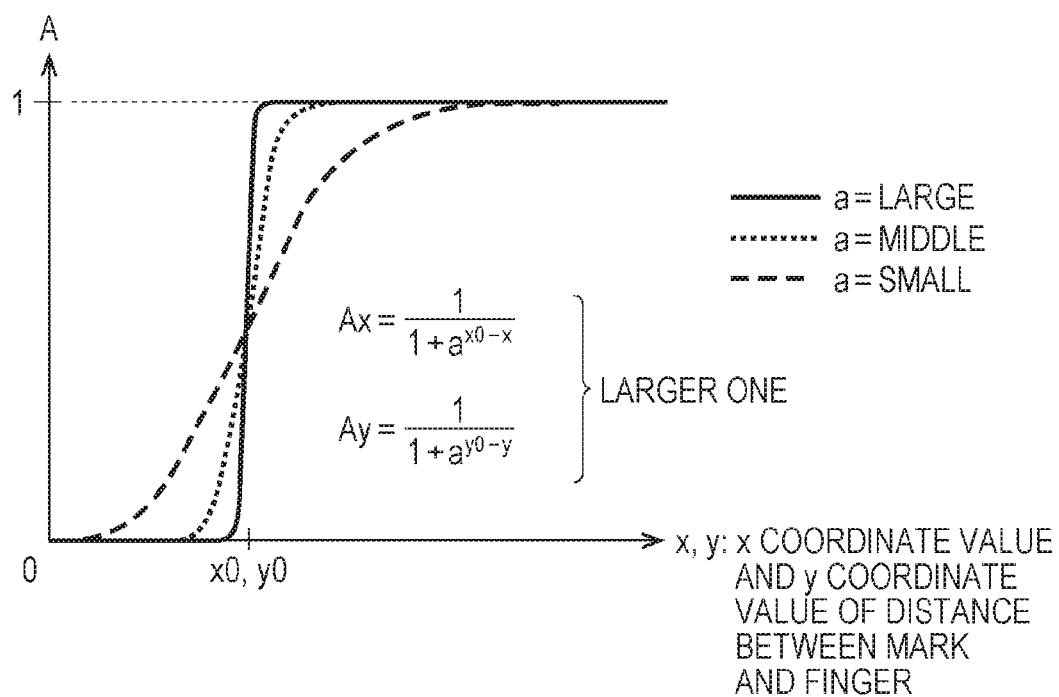

When Equation (4) is satisfied, the correlation between x (or y) and A is as illustrated in FIG. 14B, and when x (or y) is smaller than x0 (or y0) (that is, the touching means 24 is in the area surrounded by the rectangle of FIG. 14A), A is small (approaches zero) and the movement distance of the mark 23 is small, and when x (or y) is larger than x0 (or y0) (that is, the touching means 24 moves to the outside of the area surrounded by the rectangle of FIG. 14A), A is large (approaches one) and the movement distance of the mark 23 is large. In addition, by adjusting the value of the constant a, the degree of change of A when x (or y) is close to x0 (or y0) can be adjusted. For example, when the value of the constant a is set large, the value of A can be abruptly changed when x (or y) is close to x0 (or y0) as represented by the solid line in the drawing, and when the value of the constant a is set small, the value of A can be gently changed when x (or y) is close to x0 (or y0) as represented by a coarse broken line in the drawing.

Referring back to FIG. 3, the controller 11 (display controller 11c) moves the mark 23 according to the movement amount (movement position) of the mark 23 calculated by the mark position calculator 11b (S108), returns to S105 to repeat the similar processing, and when a drag operation is not detected (No in S105), ends the series of processing.

Figure 15A:
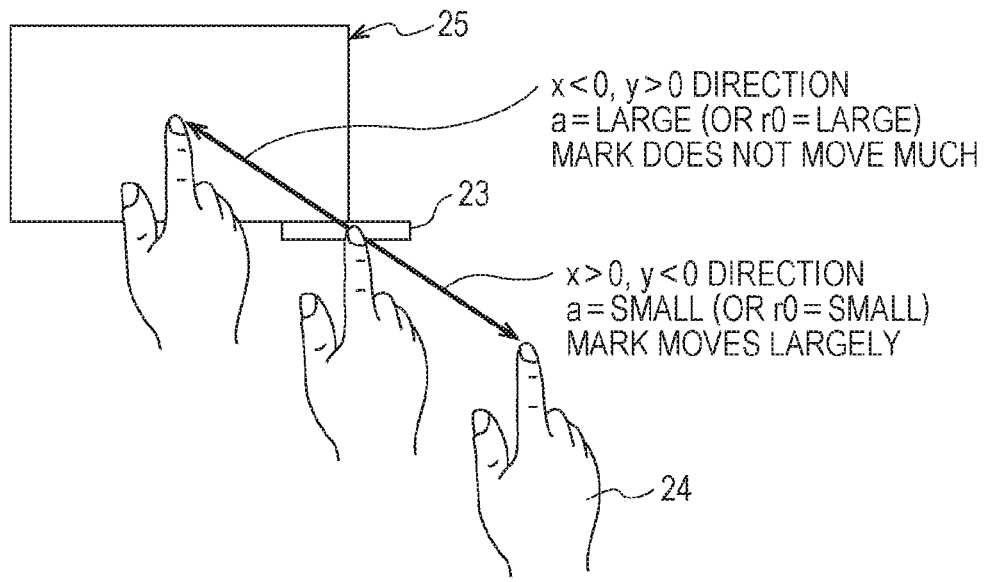
FIGS. 15A and 15B are diagrams illustrating a change in the movement amount of the mark according to a drag direction on the touch panel of the medical image display device according to the embodiment of the present invention.
Figure 15B:
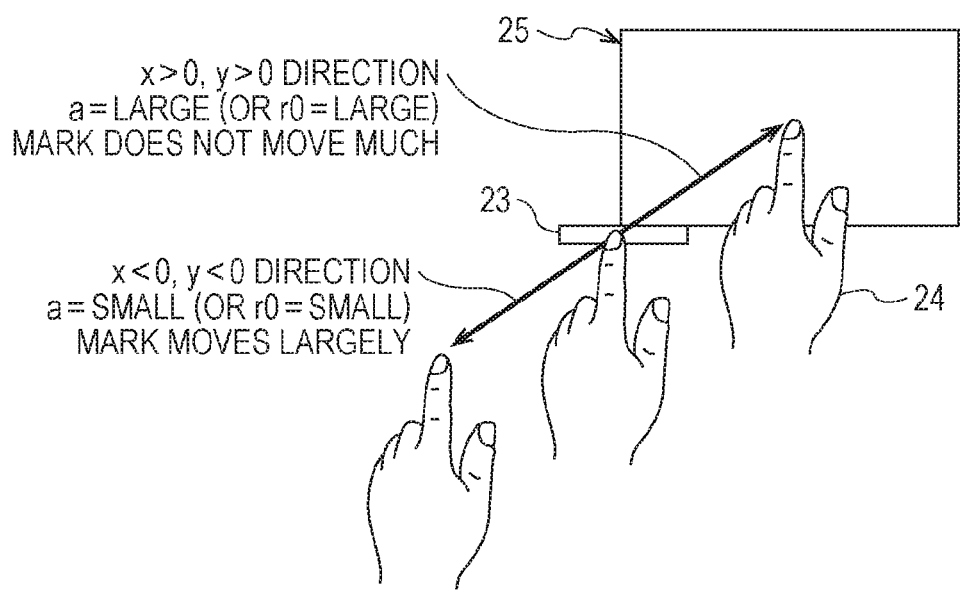

An example of the touch operation according to the present embodiment has been described above. When the mark 23 is moved toward the area of interest 25, the mark 23 is hidden by the touching means 24, and the relationship between the area of interest 25 and the mark 23 becomes difficult to recognize. In addition, depending on the dominant hand of a user, the positional relationship between the area of interest 25 and the mark 23 changes. Specifically, as illustrated in FIG. 15A, when an operator is right-handed, the movement of the touch position in the upper left direction tends to make the relationship between the area of interest 25 and the mark 23 unclear due to the touching means 24, but the movement in the lower right direction hardly causes such a problem. As illustrated in FIG. 15B, when an operator is left-handed, the movement of the touch position in the upper right direction tends to make the relationship between the area of interest 25 and the mark 23 unclear due to the touching means 24, but the movement in the lower left direction hardly causes such a problem. Therefore, a direction may be set according to the dominant hand of an operator and the values of the constant a and 10 may be set according to the direction.

Figure 4:
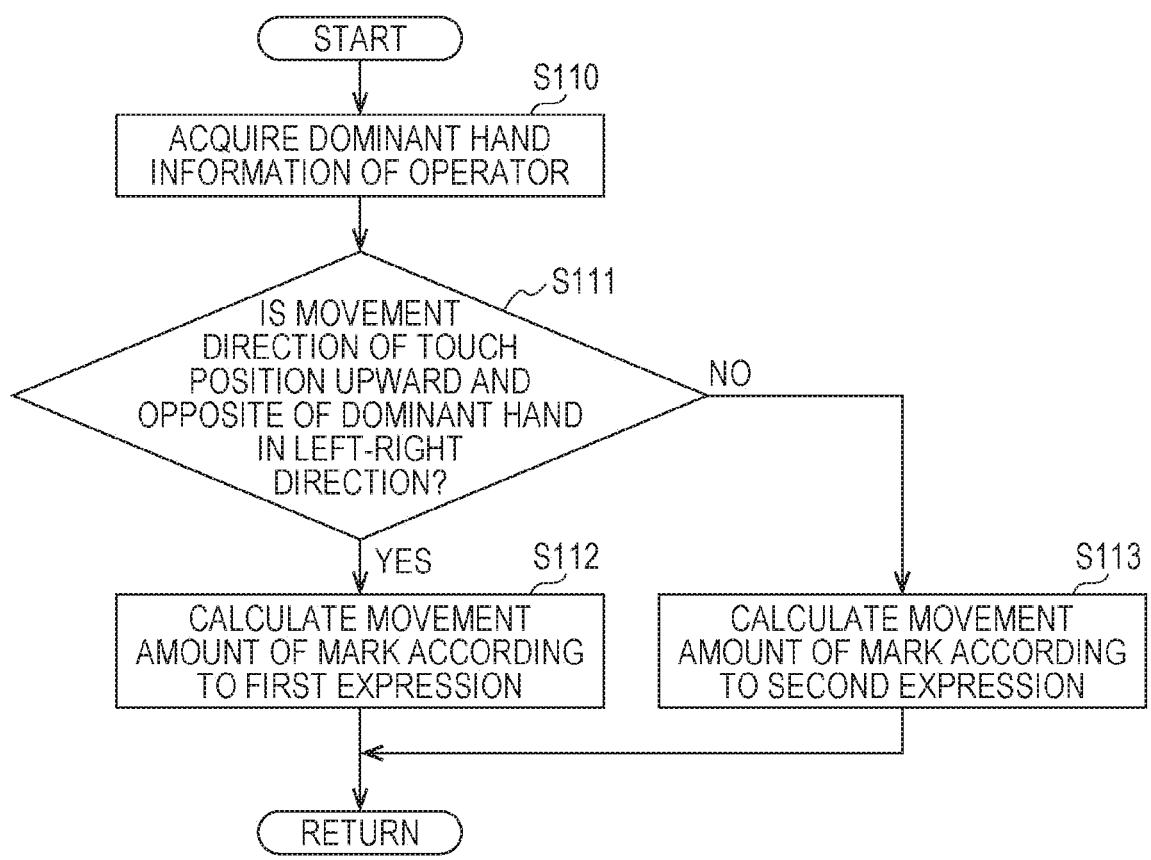
FIG. 4 is a flowchart diagram illustrating an operation (mark movement amount calculation processing) of the medical image display device according to the embodiment of the present invention.

FIG. 4 illustrates the details of the mark movement amount calculation processing (S107) in that case. An operator operates the display operation part 17 to set his/her dominant hand, and the controller 11 (operation controller 11a) acquires dominant hand information of the operator (S110). Then, the controller 11 (operation controller 11a) monitors an output signal from the display operation part 17 and determines whether the movement direction of the touch position is upward and opposite of the dominant hand in the left-right direction (S111). In a case where the movement direction of the touch position is upward and opposite of the dominant hand in the left-right direction (upper left direction in a case of right-handed, and upper right direction in a case of left-handed), the relationship between the area of interest 25 and the mark 23 becomes difficult to recognize due to the touching means 24. Therefore, the controller 11 (mark position calculator 11b) calculates the movement amount of the mark 23 according to a first expression obtained by setting the value of the constant a in the expression (2) or (4) large (or setting the value of r0 large) (S112). On the other hand, when the movement direction of the touch position is the downward direction and/or the dominant hand direction, the controller 11 (mark position calculator 11b) calculates the movement amount of the mark 23 according to a second expression obtained by setting the value of the constant a in the expression (2) or (4) small (or setting the value of r0 small) (S113).

Figure 16:
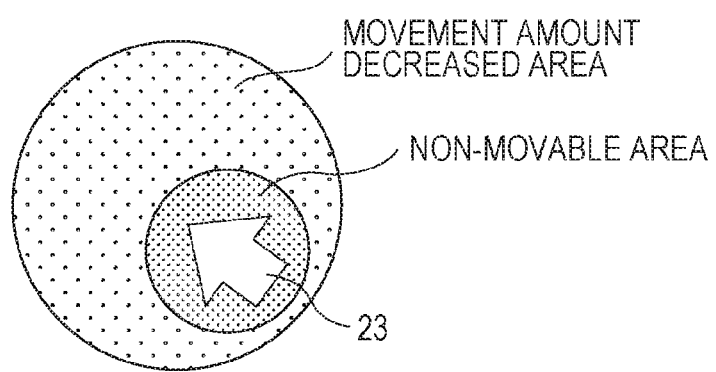
FIG. 16 is a diagram illustrating a change in the movement amount of a mark according to a distance from the mark on the touch panel of the medical image display device according to the embodiment of the present invention.

In the above description, the mark 23 is moved according to the movement amount of the touch position, but since the mark 23 is hidden by the touching means 24 at the initial stage of the drag operation, the touching means 24 has to promptly separate from the mark 23. Therefore, at the initial stage of the drag operation, it is also possible not to move the mark 23 even if the touch position is moved. In that case, for example, as illustrated in FIG. 16, a non-movable area of the mark 23 may be defined around the mark 23, and a movement amount decreased area may be further defined outside of the non-movable area, so that the degree of movement of the mark 23 may be changed depending on the distance between the mark 23 and the touching means 24.

Figure 5:
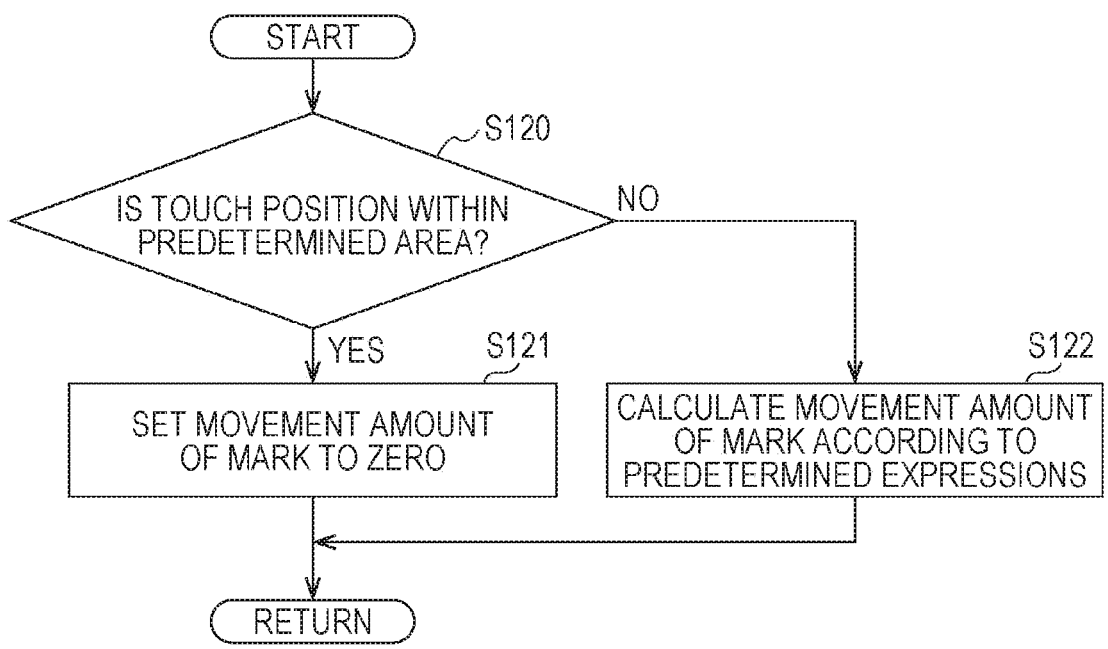
FIG. 5 is a flowchart diagram illustrating an operation (mark movement amount calculation processing) of the medical image display device according to the embodiment of the present invention.

FIG. 5 illustrates the details of the mark movement amount calculation processing (S107) in that case. First, the controller 11 (operation controller 11a) determines whether the touch position is within a predetermined area (S120). The controller 11 (mark position calculator 11b) sets the movement amount of the mark 23 to zero (S121) when the touch position is within the predetermined area (Yes in S120), and calculates the movement amount of the mark 23 according to predetermined expressions ((1) and (2), or (3) and (4)) (S122) when the touch position is out of the predetermined area (No in S120).

In the above description, by making the movement amount of the mark 23 smaller than the movement amount of the touch position, the touching means 24 is separated from the mark 23 so that the relationship between the area of interest 25 and the mark 23 can be grasped. However, the touching means 24 hides the mark 23 in an area close to the touch position as the start point of the drag operation, which is inconvenient when accurate operation is desired. In that case, it is also possible to set a position away from the mark 23 as a start point of the drag operation, and the mark 23 is moved according to the movement trajectory of the touch position. In this way, the relationship between the area of interest 25 and the mark 23 can be grasped.

Figure 6:
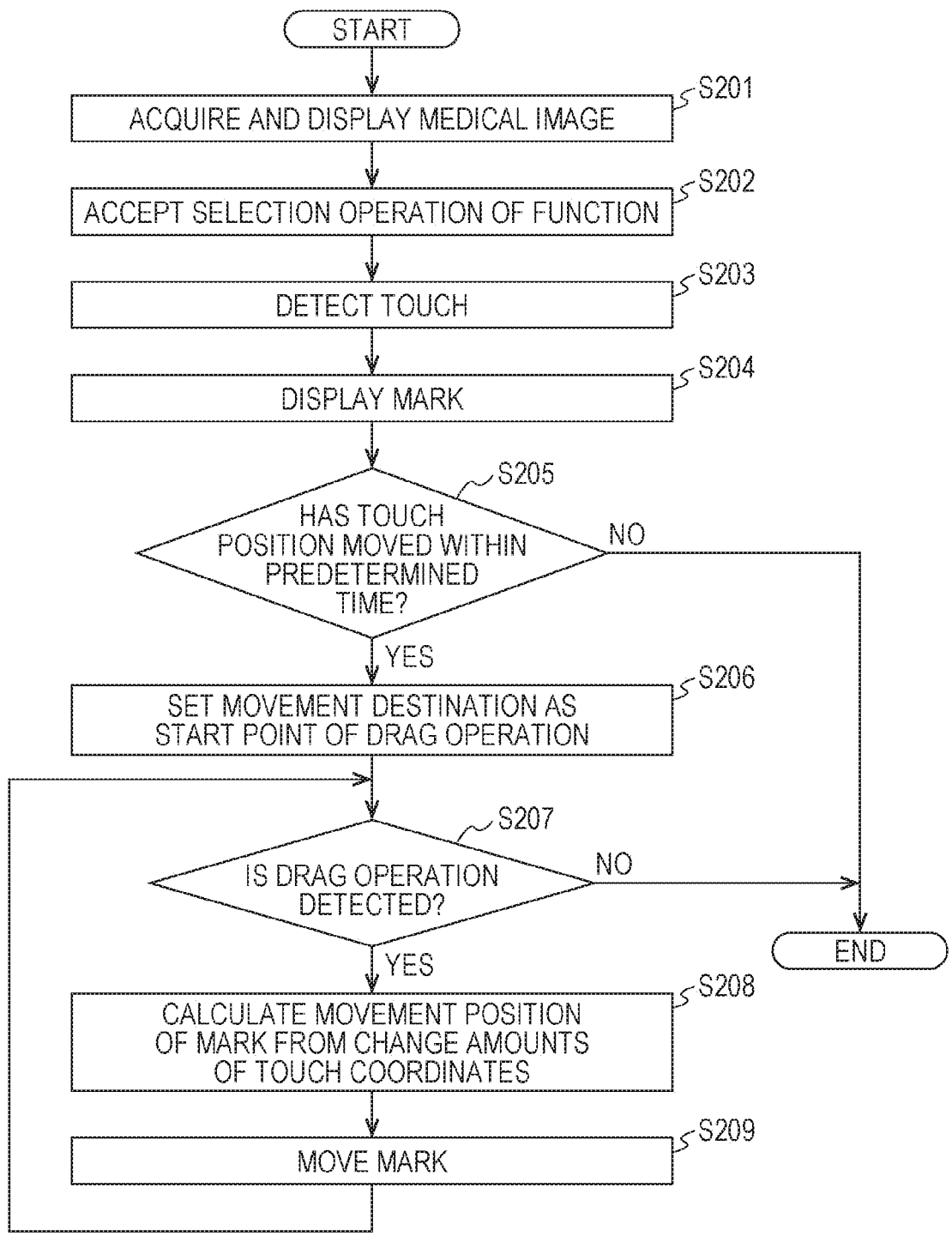
FIG. 6 is a flowchart diagram illustrating the operation of the medical image display device according to the embodiment of the present invention.

FIG. 6 illustrates the operation in that case. First, similarly to FIG. 3, the controller 11 (display controller 11c) first acquires a medical image obtained by measuring a patient or the like, and displays the display screen 20 as illustrated in FIG. 8 on the display operation part 17 (S201). Next, the controller 11 (operation controller 11a) accepts a function selection operation on the setting field 22 of the display screen 20 or the like (S202). Here, a selection operation of a measurement function for measuring various kinds of information of a medical image is accepted.

The controller 11 (operation controller 11a) then monitors an output signal from the display operation part 17, and upon detection of a touch operation on the image display field 21 of the display screen 20 by an operator (S203), the controller 11 (display controller 11c) displays the mark 23 corresponding to the function selected in S202 (here, a caliper corresponding to the measurement function) at the touch position (S204). In the present embodiment, when a touch operation is detected, a mark 23 is displayed at the touch position. However, similarly to FIG. 3, when a function is selected, a mark may be displayed at a predetermined position.

Next, the controller 11 (operation controller 11a) determines whether the touch position has moved within a predetermined time (S205). When the touch position has not moved within the predetermined time (No in S205), the controller 11 ends the series of processing, and when the touch position has moved within the predetermined time (Yes in S205), the controller 11 (operation controller 11a) sets the movement destination as a start point of a drag operation (S206).

Next, the controller 11 (operation controller 11a) monitors an output signal from the display operation part 17, determines whether a drag operation by an operator is detected (S207), and when a drag operation is detected (Yes in S207), the controller 11 (mark position calculator 11b) calculates a movement position of the mark 23 based on a change amounts of coordinates of the touch position (S208). Then, the controller 11 (display controller 11c) moves the mark 23 by the change amounts of the coordinates of the touch position based on the movement position of the mark 23 calculated by the mark position calculator 11b (S209), returns to S207 to repeat the similar processing, and when a drag operation is not detected (No in S207), ends the series of processing.

FIGS. 17A to 17C schematically illustrate this operation. In a case where an operator touches the mark 23 to select it as illustrated in FIG. 17A and moves the touching means 24 within a predetermined time as illustrated in FIG. 17B, the movement destination is set as a start point of a drag operation. Then, as illustrated in FIG. 17C, when a drag operation is detected, the mark 23 is moved according to the movement amount of the touch position.

Figure 7:
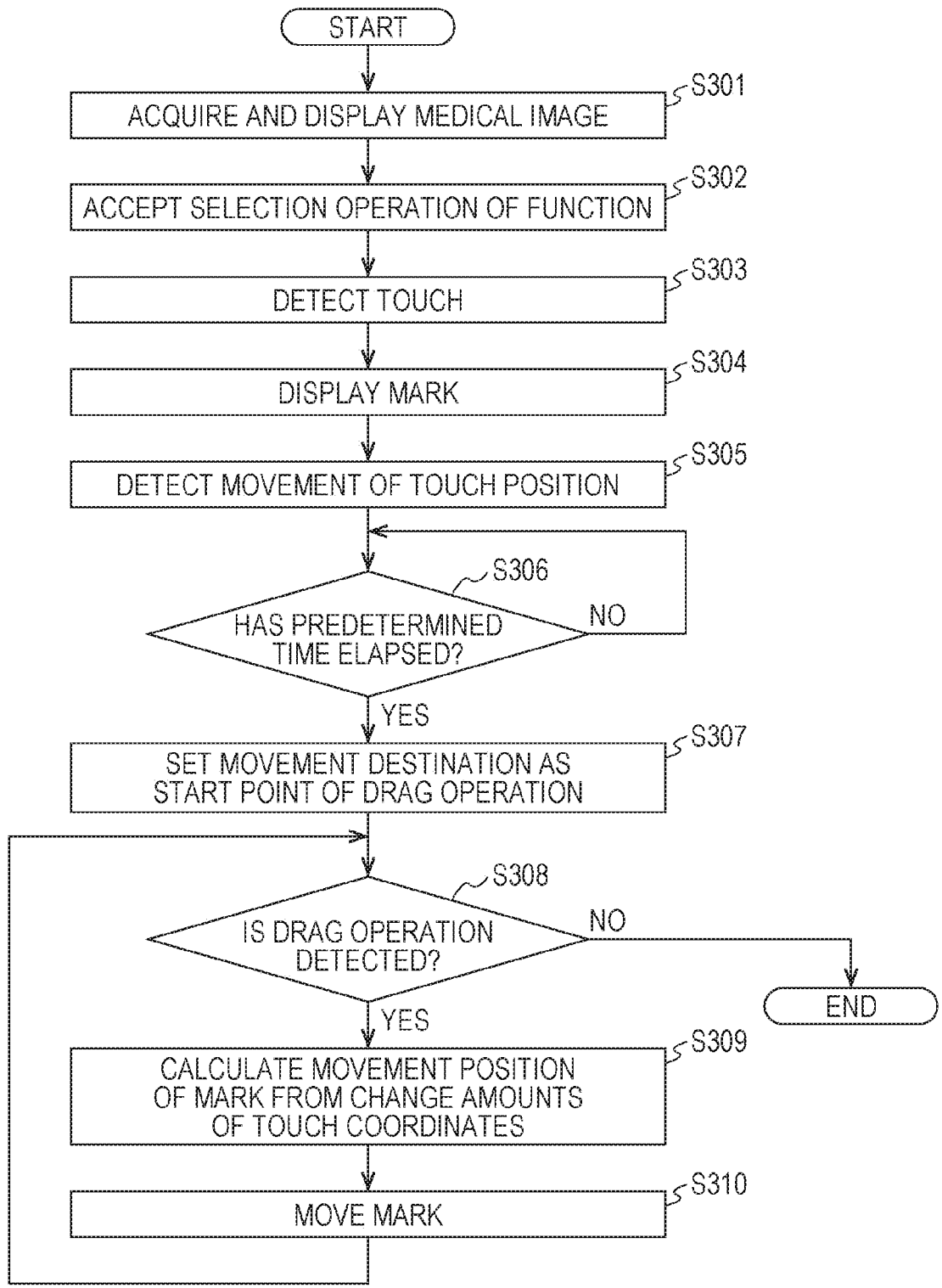
FIG. 7 is a flowchart diagram illustrating an operation of the medical image display device according to the embodiment of the present invention.
Figures 8, 9:
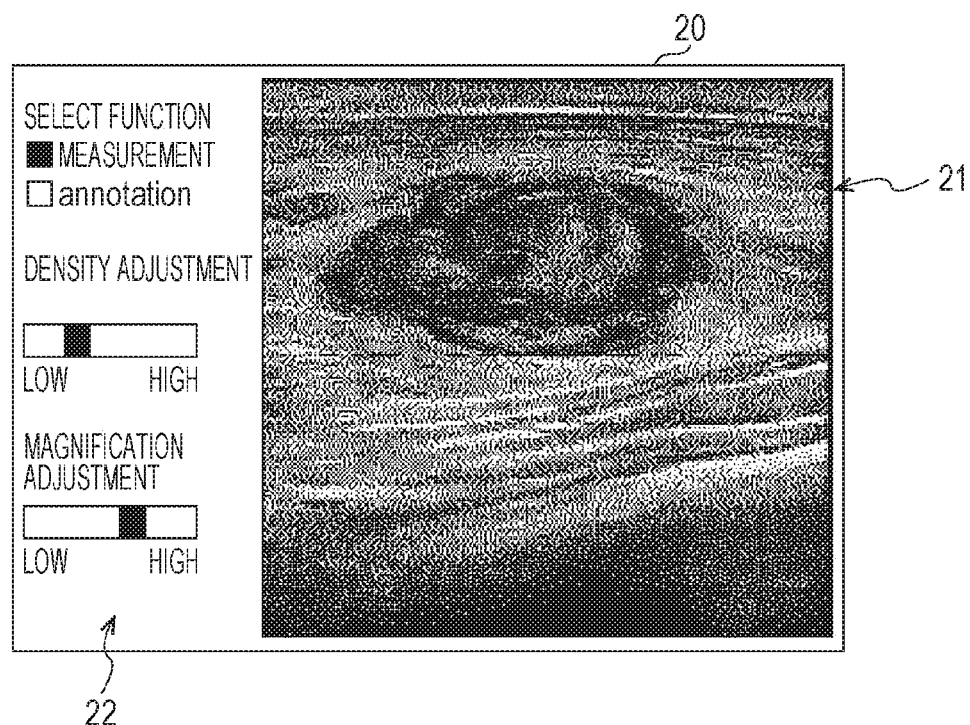
FIG. 8 is an example of a display screen displayed on a touch panel of the medical image display device according to the embodiment of the present invention.
FIG. 9 is an example of marks corresponding to functions of the medical image display device according to the embodiment of the present invention.

FIG. 7 illustrates another operation. First, similarly to FIG. 3, the controller 11 (display controller 11c) first acquires a medical image obtained by measuring a patient or the like, and displays the display screen 20 as illustrated in FIG. 8 on the display operation part 17 (S301). Next, the controller 11 (operation controller 11a) accepts a function selection operation on the setting field 22 of the display screen 20 or the like (S302). Also in this operation, a selection operation of a measurement function for measuring various kinds of information of a medical image is accepted.

The controller 11 (operation controller 11a) then monitors an output signal from the display operation part 17. Upon detection of a touch operation on the image display field 21 of the display screen 20 by an operator (S303), the controller 11 (display controller 11c) displays the mark corresponding to the function selected in S302 (also in this operation, a caliper corresponding to the measurement function) at the touch position (S304). In the present embodiment, when a touch operation is detected, a mark 23 is displayed at the touch position. However, similarly to FIG. 3, when a function is selected, a mark may be displayed at a predetermined position.

Next, the controller 11 (operation controller 11a) monitors an output signal from the display operation part 17, and upon detection of movement of the touch position (S305), determines whether the predetermined time has elapsed while the touch position does not move (S306). When the predetermined time has elapsed (Yes in S306), the controller 11 (operation controller 11a) sets the movement destination as a start point of a drag operation (S307).

Next, the controller 11 (operation controller 11a) monitors an output signal from the display operation part 17, and determines whether a drag operation by an operator is detected (S308). Upon detection of drag operation (Yes in S308), the controller 11 (mark position calculator 11b) calculates a movement position of the mark 23 based on a change amounts of coordinates of the touch position (S309). Then, the controller 11 (display controller 11c) moves the mark 23 by the change amounts of the coordinates of the touch position based on the movement position of the mark 23 calculated by the mark position calculator 11b (S310), returns to S308 to repeat the similar processing, and when a drag operation is not detected (No in S308), ends the series of processing.

FIGS. 18A to 18C schematically illustrate this operation. In a case where an operator touches the mark 23 to select it as illustrated in FIG. 18A and moves the touching means 24 illustrated in FIG. 18B, and thereafter a predetermined time has elapsed while the touching means 24 stops, the movement destination is set as a start point of a drag operation. Then, as illustrated in FIG. 18C, when a drag operation is detected, the mark 23 is moved according to the movement amount of the touch position.

Figure 19:
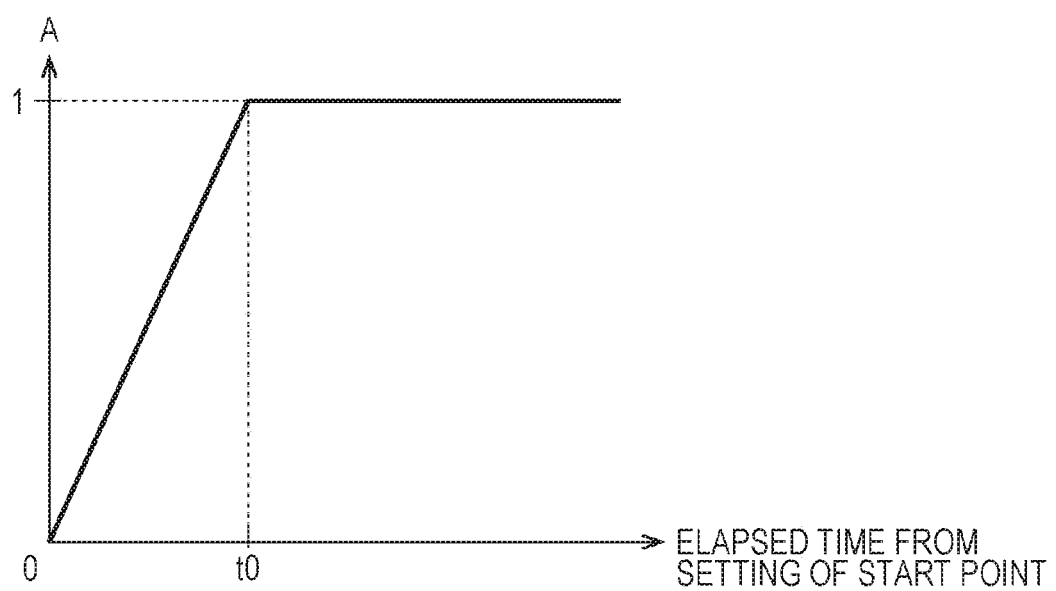
FIG. 19 is a diagram illustrating a change in a movement amount of the mark (the caliper when the measurement function is selected) on the touch panel of the medical image display device according to the embodiment of the present invention.

When the mark 23 is moved according to the movement amount of the touch position after setting the start point of the drag operation, the ratio of the movement amount of the touch position to the movement amount of the mark 23 may be constant. However, at the initial stage of the drag operation, it may be difficult to recognize the relationship between the area of interest 25 and the mark 23 due to the touching means 24 because the touching means 24 is close to the mark 23 at the initial stage. In such a case, as illustrated in FIG. 19, the constant A is made small (so that the mark 23 does not move too much) from the time when a start point of a drag operation is set to a predetermined time (t0), and after the predetermined time elapses, the constant A may be made constant (the mark 23 is moved largely according to the movement of the touch position).

Figure 20A:
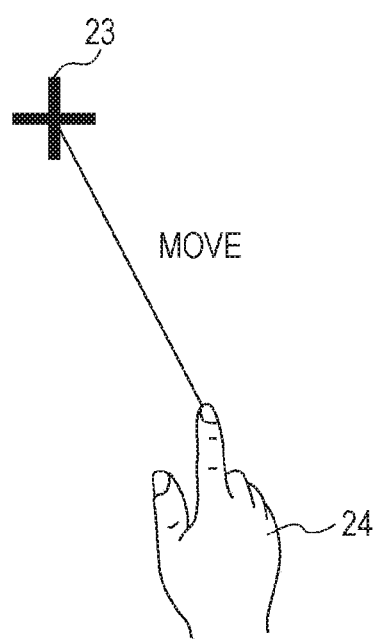
FIGS. 20A and 20B are display examples of the mark (the caliper when the measurement function is selected) on the touch panel of the medical image display device according to the embodiment of the present invention.
Figure 20B:
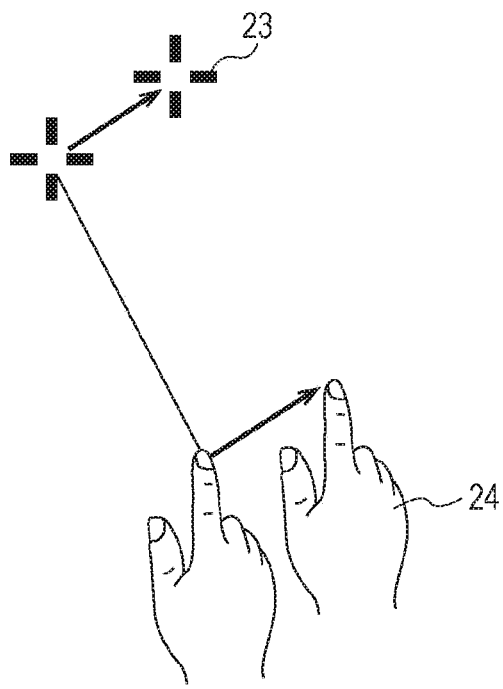

In addition, in the cases of FIGS. 17A to 17C and FIGS. 18A to 18C, it is difficult to recognize whether a start point of a drag operation is set (whether the touch position has moved within the predetermined time or the predetermined time has elapsed since the touch position was moved). Thus, when the start point of the drag operation is set, the display form of the mark 23 may be changed. For example, when the touch position does not move within the predetermined time or when the predetermined time has not elapsed since the touch position moved, the mark 23 cannot be moved. Thus, the display form of the mark 23 may not be changed as illustrated in FIG. 20A. On the other hand, when the touch position has moved within the predetermined time or when the predetermined time has elapsed since the touch position moved, the mark 23 can be moved. Thus, the display form of the mark 23 may be changed as illustrated in FIG. 20B. Alternatively, when the touch position does not move within the predetermined time or when the predetermined time has not elapsed since the touch position moved, the display form of the mark 23 may be changed to flickering of the mark 23 or the like.

As described above, upon detection of a drag operation on the mark 23 corresponding to a selected function, the medical image display device 10 including the touch panel for displaying a medical image calculates a movement position of the mark 23 such that the movement trajectory of the touch position and the movement trajectory of the mark 23 are different from each other based on the coordinates of the touch position in the drag operation, and moves the mark 23 on the medical image based on the calculated movement position. Thus, the visibility of an object (the mark 23 or the medical image in the vicinity of the mark 23) can be improved and the mark 23 can be accurately operated on the medical image.

It should be noted that the present invention is not limited to the above-described embodiment, and the configuration and control contents of the medical image display device 10 can be appropriately modified without departing from the spirit of the present invention.

For example, in the embodiment described above, the annotation function and the measurement function are exemplified as functions of the medical image display device 10, but the touch operation control method of the present invention can be similarly applied to other functions.

In the embodiment described above, the arrow mark, the probe mark, and the caliper are exemplified as the mark 23, but the touch operation control method of the present invention may be similarly applied to an object such as an arbitrary mark corresponding to an arbitrary function.

In addition, the expressions for calculating the movement distance of the mark 23 corresponding to the annotation function are presented an example, and an arbitrary expression that can be set such that the movement amount of the mark 23 becomes small when the mark 23 and the touching means 24 (finger) are close to each other can be used.

The present invention is applicable to a medical image display device having a touch panel that displays a medical image, a touch operation control program that controls a touch operation on the touch panel of the medical image display device, a recording medium having the touch operation control program stored therein, and a touch operation control method.

Although embodiments of the present invention have been described and illustrated in detail, the disclosed embodiments are made for purposes of illustration and example only and not limitation. The scope of the present invention should be interpreted by terms of the appended claims

What is claimed is:
1. A medical image display device, comprising:
a display operation part having a touch panel; and
a hardware processor that displays the medical image on the display operation part and displays a mark on the medical image, the mark corresponding to a function selected from a plurality of functions on the display operation part,
determines whether a drag operation on the mark on the touch panel by an operator is detected,
calculates a movement position of the mark according to a rule corresponding to at least one of the selected function, an object, and a user, based on coordinates of a touch position in the drag operation; and
causes the display operation part to move the mark on the medical image based on the calculated movement position, wherein
the hardware processor calculates the movement position of the mark such that a movement trajectory of the touch position and a movement trajectory of the mark are different from each other,
when a second function is selected, the hardware processor sets a position associated with the touch position on the mark as a start point of the drag operation,
the hardware processor calculates the movement position of the mark such that the mark moves corresponding to movement of the touch position in the drag operation, and
the hardware processor determines whether the touch position has moved before a predetermined time elapses from detection of touch to the mark, and when the touch position moves before the predetermined time elapses, the hardware processor sets a movement destination as the start point of the drag operation.

2. The medical image display device according to claim 1, wherein the movement position of the mark is calculated such that a length of a movement trajectory of the touch position and a length of a movement trajectory of the mark are different from each other.

3. The medical image display device according to claim 1, wherein
when a first function is selected, the hardware processor sets the touch position on the mark as a start point of the drag operation, and
the hardware processor calculates the movement position of the mark such that a movement amount of the mark is smaller than a movement amount of the touch position.

4. The medical image display device according to claim 3, wherein
the hardware processor calculates the movement position of the mark such that the movement amount of the mark is smaller than the movement amount of the touch position when the touch position is within a predetermined area around a center of the mark.

5. The medical image display device according to claim 3, wherein
the hardware processor accepts a setting operation of a dominant hand of an operator and detects a moving direction of the touch position, and
the hardware processor calculates the movement position of the mark such that the movement amount of the mark is smaller than the movement amount of the touch position when the touch position moves upward and opposite of the dominant hand in a left direction or a right direction on the touch panel.

6. A medical image display device, comprising:
a display operation part having a touch panel; and
a hardware processor that displays the medical image on the display operation part and displays a mark on the medical image, the mark corresponding to a function selected from a plurality of functions on the display operation part,
determines whether a drag operation on the mark on the touch panel by an operator is detected,
calculates a movement position of the mark according to a rule corresponding to at least one of the selected function, an object, and a user, based on coordinates of a touch position in the drag operation; and
causes the display operation part to move the mark on the medical image based on the calculated movement position, wherein
the hardware processor calculates the movement position of the mark such that a movement trajectory of the touch position and a movement trajectory of the mark are different from each other,
when a second function is selected, the hardware processor sets a position associated with the touch position on the mark as a start point of the drag operation,
the hardware processor calculates the movement position of the mark such that the mark moves corresponding to movement of the touch position in the drag operation, and
the hardware processor determines whether the touch position has not moved before a predetermined time elapses from detection of movement of a touch position to the mark, and when the touch position has not moved before the predetermined time elapses, the hardware processor sets a movement destination as the start point of the drag operation.

7. The medical image display device according to claim 6, wherein
when a first function is selected, the hardware processor sets the touch position on the mark as a start point of the drag operation, and
the hardware processor calculates the movement position of the mark such that a movement amount of the mark is smaller than a movement amount of the touch position.

8. The medical image display device according to claim 7, wherein
the hardware processor calculates the movement position of the mark such that the movement amount of the mark is smaller than the movement amount of the touch position when the touch position is within a predetermined area around a center of the mark.

9. The medical image display device according to claim 7, wherein
the hardware processor accepts a setting operation of a dominant hand of an operator and detects a moving direction of the touch position, and
the hardware processor calculates the movement position of the mark such that the movement amount of the mark is smaller than the movement amount of the touch position when the touch position moves upward and opposite of the dominant hand in a left direction or a right direction on the touch panel.

10. A medical image display device, comprising:
a display operation part having a touch panel; and
a hardware processor that displays the medical image on the display operation part and displays a mark on the medical image, the mark corresponding to a function selected from a plurality of functions on the display operation part,
determines whether a drag operation on the mark on the touch panel by an operator is detected,
calculates a movement position of the mark according to a rule corresponding to at least one of the selected function, an object, and a user, based on coordinates of a touch position in the drag operation; and
causes the display operation part to move the mark on the medical image based on the calculated movement position, wherein
the hardware processor calculates the movement position of the mark such that a movement trajectory of the touch position and a movement trajectory of the mark are different from each other,
when a second function is selected, the hardware processor sets a position associated with the touch position on the mark as a start point of the drag operation,
the hardware processor calculates the movement position of the mark such that the mark moves corresponding to movement of the touch position in the drag operation, and
the hardware processor calculates the movement position of the mark such that the movement amount of the mark is smaller than the movement amount of the touch position before a predetermined time elapses from setting of the start point of the drag operation.

11. The medical image display device according to claim 10, wherein
when a first function is selected, the hardware processor sets the touch position on the mark as a start point of the drag operation, and
the hardware processor calculates the movement position of the mark such that a movement amount of the mark is smaller than a movement amount of the touch position.

12. The medical image display device according to claim 11, wherein
the hardware processor calculates the movement position of the mark such that the movement amount of the mark is smaller than the movement amount of the touch position when the touch position is within a predetermined area around a center of the mark.

13. The medical image display device according to claim 11, wherein
the hardware processor accepts a setting operation of a dominant hand of an operator and detects a moving direction of the touch position, and
the hardware processor calculates the movement position of the mark such that the movement amount of the mark is smaller than the movement amount of the touch position when the touch position moves upward and opposite of the dominant hand in a left direction or a right direction on the touch panel.

14. A non-transitory recording medium storing a computer readable program that runs on a medical image display device having a display operation part with a touch panel that displays a medical image, the program causing a hardware processor of the medical image display device to perform:
causing the display operation part to display the medical image;
displaying a mark corresponding to the selected function on the medical image, the mark corresponding to a function selected from a plurality of functions on the display operation part;
detecting a drag operation on the mark;
calculating a movement position of the mark according to a rule corresponding to at least one of the selected function, an object, and a user based on coordinates of a touch position in the drag operation; and
moving the mark on the medical image based on the calculated movement position, wherein
in the calculating, the hardware processor calculates the movement position of the mark such that a movement trajectory of the touch position and a movement trajectory of the mark are different from each other,
when a second function is selected in the accepting an operation for selecting a desired function, the hardware processor sets a position associated with the touch position on the mark as a start point of the drag operation in the detecting a drag operation on the mark,
the hardware processor calculates the movement position of the mark such that the mark moves corresponding to movement of the touch position in the calculating a movement position, and
the hardware processor determines whether the touch position has moved before a predetermined time elapses from detection of touch to the mark, and when the touch position moves before the predetermined time elapses, the hardware processor sets a movement destination as the start point of the drag operation in the detecting a drag operation on the mark.

15. The non-transitory recording medium storing a computer readable program according to claim 14, wherein
when a first function is selected in the accepting an operation for selecting a desired function, the hardware processor sets the touch position on the mark as a start point of the drag operation in the detecting, and
the hardware processor calculates the movement position of the mark such that a movement amount of the mark is smaller than a movement amount of the touch position in the calculating a movement position.

16. The non-transitory recording medium storing a computer readable program according to claim 15, wherein
in the calculating a movement position, the hardware processor calculates the movement position of the mark such that the movement amount of the mark is smaller than the movement amount of the touch position when the touch position is within a predetermined area around a center of the mark.

17. The non-transitory recording medium storing a computer readable program according to claim 15, wherein
the touch operation control program further causes the hardware processor of the medical image display device to perform accepting a setting operation of a dominant hand of an operator,
the hardware processor detects a moving direction of the touch position in the detecting a drag operation on the mark, and
the hardware processor calculates the movement position of the mark such that the movement amount of the mark is smaller than the movement amount of the touch position when the touch position moves upward and opposite of the dominant hand in a left direction or a right direction on the touch panel in the calculating a movement position.

18. The non-transitory recording medium storing a computer readable program according to claim 14, wherein the hardware processor determines whether the touch position has not moved before a predetermined time elapses from detection of movement of a touch position to the mark, and when the touch position has not moved before the predetermined time elapses, the hardware processor sets a movement destination as the start point of the drag operation in the detecting a drag operation on the mark.

19. The non-transitory recording medium storing a computer readable program according to claim 14, wherein the hardware processor calculates the movement position of the mark such that the movement amount of the mark is smaller than the movement amount of the touch position before a predetermined time elapses from setting of the start point of the drag operation in the calculating a movement position.

20. A touch operation control method in a medical image display device having a touch panel for displaying a medical image, the method comprising:
causing the touch panel to display the medical image;
displaying a mark corresponding to the selected function on the medical image, the mark corresponding to a function selected from a plurality of functions on the display operation part;
detecting a drag operation on the mark;
calculating a movement position of the mark according to a rule corresponding to at least one of the selected function, an object, and a user based on coordinates of a touch position in the drag operation; and
moving the mark on the medical image based on the calculated movement position, wherein
in the calculating, the hardware processor calculates the movement position of the mark such that a movement trajectory of the touch position and a movement trajectory of the mark are different from each other,
when a second function is selected in the accepting an operation for selecting a desired function, the hardware processor sets a position associated with the touch position on the mark as a start point of the drag operation in the detecting a drag operation on the mark,
the hardware processor calculates the movement position of the mark such that the mark moves corresponding to movement of the touch position in the calculating a movement position of the mark, and the hardware processor determines whether the touch position has moved before a predetermined time elapses from detection of touch to the mark, and when the touch position moves before the predetermined time elapses, the hardware processor sets a movement destination as the start point of the drag operation in the detecting a drag operation on the mark.

21. The touch operation control method according to claim 20, wherein when a first function is selected in the accepting an operation for selecting a desired function, the hardware processor sets the touch position on the mark as a start point of the drag operation in the detecting a drag operation on the mark, and the hardware processor calculates the movement position of the mark such that a movement amount of the mark is smaller than a movement amount of the touch position in the calculating a movement position of the mark.

22. The touch operation control method according to claim 21, wherein in the calculating a movement position of the mark, the hardware processor calculates the movement position of the mark such that the movement amount of the mark is smaller than the movement amount of the touch position when the touch position is within a predetermined area around a center of the mark.

23. The touch operation control method according to claim 21 further comprising accepting a setting operation of a dominant hand of an operator, wherein the hardware processor detects a moving direction of the touch position in the detecting a drag operation on the mark, and the hardware processor calculates the movement position of the mark such that the movement amount of the mark is smaller than the movement amount of the touch position when the touch position moves upward and opposite of the dominant hand in a left direction or a right direction on the touch panel in the calculating a movement position of the mark.

24. The touch operation control method according to claim 20, wherein the hardware processor determines whether the touch position has not moved before a predetermined time elapses from detection of movement of a touch position to the mark, and when the touch position has not moved before the predetermined time elapses, the hardware processor sets a movement destination as the start point of the drag operation in the detecting a drag operation on the mark.

25. The touch operation control method according to claim 20, wherein the hardware processor calculates the movement position of the mark such that the movement amount of the mark is smaller than the movement amount of the touch position before a predetermined time elapses from setting of the start point of the drag operation in the calculating a movement position of the mark.

* * * * *